(12) United States Patent
Brown

(10) Patent No.: US 8,399,031 B1
(45) Date of Patent: Mar. 19, 2013

(54) COMPOSITIONS AND METHODS FOR RESTORING PULMONARY FUNCTION

(76) Inventor: Gerald Brown, Piedmont, AL (US)

( * ) Notice: Subject to any disclaimer, the term of this patent is extended or adjusted under 35 U.S.C. 154(b) by 0 days.

(21) Appl. No.: 12/756,012

(22) Filed: Apr. 7, 2010

(51) Int. Cl.
*A61K 36/736* (2006.01)
*A61K 36/61* (2006.01)
*A61K 36/00* (2006.01)

(52) U.S. Cl. .................. 424/735; 424/742; 424/725

(58) Field of Classification Search ................ None
See application file for complete search history.

(56) References Cited

PUBLICATIONS

BBC news. Asthma risk "greater for smokers". Retrieved from the internet on Nov. 18, 2011. <http://news.bbc.co.uk/2/hi/health/3950645.stm>. Oct. 24, 2004. 3 pages.*
CCOHS. Asthma. Retrieved from the internet on Nov. 18, 2011. <http://www.ccohs.ca/oshanswers/diseases/asthma.html>. Feb. 8, 2005. 8 pages.*
Church. West Virginia Medicinal Plants, Trees & Shrubs, A Field Guide. Lulu..com. 2004. p. 31.*
Rahman. Studies in Natural Products Chemistry: Bioactive Natural Products (part I) vol. 32. 2005. pp. 286-287.*
Scudder. The American Eelectic materia medica and therapeutics. 1885. p. 572.*
Herbal Applications to Conditions & Body Organs, http://www.viablehealth.com/herb/herbs09.htm , Mar. 13, 2010, 16 pages.

* cited by examiner

*Primary Examiner* — Christopher R. Tate
(74) *Attorney, Agent, or Firm* — Nancy Lord

(57) ABSTRACT

This invention relates to compositions and methods that restore pulmonary function, preferably inhibiting or arresting the constriction of the bronchial tubes when administered to mammals, including humans. The pulmonary restorative composition for improving respiratory health comprises an effective amount of *Gnaphalium obtusifolium* L., more commonly known as rabbit tobacco, sweet everlasting and other historical names; *Liquidambar*, more commonly known as sweet gum; and *Verbascum*, more commonly known as mullein. Optionally, the composition may include at least of one additional herbal nutrient selected from the group *Prunus avium*, more commonly known as wild cherry; *Althaea officinalis*, more commonly known as marshmallow or mallow; *Prunus amygdalus*, more commonly known as peach; and *Eucalyptus*; and may include glucose. Also disclosed are methods for restoring or maintaining pulmonary function by the administration of the composition of the invention.

8 Claims, No Drawings

US 8,399,031 B1

COMPOSITIONS AND METHODS FOR RESTORING PULMONARY FUNCTION

FIELD OF INVENTION

This invention relates to compositions and methods that restore pulmonary function, preferably inhibiting or arresting the constriction of the bronchial tubes when administered to mammals, including humans.

BACKGROUND OF THE INVENTION

The present invention relates generally to compositions and methods for treating pulmonary dysfunction; more particularly, it relates to methods and compositions for treating or preventing constriction of the bronchial tubes whereby the many and varied problems associated with the disease can be prevented, arrested, substantially alleviated or cured.

This inventor has discovered that the combined use of these herbs produces a composition that is remarkably effective in restoring pulmonary function. Previous inventions have disclosed two or more of these herbs in Markush groups for various nutritional products for other purposes, mostly in topical formulations and, in regards to the *Prunus* species of cherry and peach, as flavorings for medicinal foods. For instance, U.S. Pat. No. 6,342,208, to Hyldgaard describes such a group for an oil-in-water emulsion for treating skin disorders; and U.S. Pat. No. 6,045,779, to Meuller, discloses *Prunus amygdalus* (peach) and *Althea officinalis* (mallow) in a Markush group for a skin and hair aerosol foam preparation. U.S. Pat. No. 6,399,114, to Foreman, describes a nutritional system for nervous system disorders that combines *Verbascum* (mullein) as a Vitamin C source with *Althea* (mallo) as a source of magnesium sources, but does not teach their use in the restoration or maintenance of pulmonary function. U.S. Pat. No. 6,210,738, to Chen, describes a combination of *Verbascum* (mullein) and winter cherry among numerous nutrients to use in a freeze-dried ginseng berry tea as "natural health promoting ingredients" but the teachings of Chen are not directed to pulmonary function. U.S. Pat. No. 4,581,230, to Grollier, teaches the combination of cherry flowers (not bark) with water soluble portions or mullein or marsh mallow in cosmetic composition for the treatment of the hair and skin. Similarly, U.S. Pat. No. 6,403,654 discloses the combined use of mallow and eucalyptus, but it does not disclose the combination with *Gnaphalium obtusifolim* L., *Liquidambar*, or *Verbascum*, and the composition is used for the treatment for psoriasis. *Verbascum* and *Eucalyptus* are taught by Blount in U.S. Pat. No. 6,287,567 in a method of making an herbal drink. Golz-Berner, in U.S. Pat. No. 6,426,080 and others, utilizes various *Prunus* species and *Arecola* fruits in cosmetic preparations of active substances with high protection factor against free radicals. The combined suggestion of cherry and peach as optional flavorings is ubiquitous in the data base as various nutritional foods, drinks and the like.

No inventor has disclosed the combination of *Gnaphalium obtusifolim* L with *Liquidambar*, with or without *Verbascum*, for restoring or maintaining pulmonary function in mammals.

*Gnaphalium obtusifolim* L.

*Gnaphalium obtusifolium* L is also known as Sweet Everlasting, Cudweed, Old Field Balsam, Sweet White Balsam, Indian Posy, Life of Man, Poverty Weed, and Fussy Gussy. It was used extensively by Native Americans for a wide variety of ailments, including asthma, but little is known as to its mechanism of action. James Mooney (1886, 325), who studied extensively among the Eastern Cherokee, wrote about the use of *Gnaphalium decurrens*, winged cudweed or winged life everlasting. This species, now known as *G. viscosum*, is identical to *G. obtusifolium* except that the leaves are stalkless. It is probable that the two were not differentiated by the Cherokees. He writes that it is "considered one of their most valuable medical plants." The decoction is drunk for colds and it is used in the sweat lodge. As the next source notes, it is also diaphoretic. Several books by modern Cherokee authors mention the use of rabbit tobacco, and identify rabbit tobacco as *Gnaphalium obtusifolium* and record the following uses:

Decoction for colds; use with carolina vetch [*Vicia caroliniana*] for rheumatism; sweat bath for various diseases; warm liquid is blow down through joy-pye-weed stem for clogged throat (diphtheria); ingredient in medicine for local pains, muscular cramps, and twitching; chew for sore mouth or throat; smoke for asthma; cough syrup.

Wood, Mathew, Reg. Herbalist, AN INTUITIVE STUDY OF RABBIT TOBACCO, originally presented as a paper at the Scottish School of Herbal Medicine (2007).

*Liquidambar*

The tree received its name for the sweet taste and gummy feel of its sap. Early Pioneers used to make chewing gum. The Sweet gum plant is from the genus *Liquidambar* and is a member of the deciduous hardwoods or Hamamelidaceae. The North American species is native to Connecticut, south to New York to Florida, southern Ohio, Indiana, Illinois, Missouri to Texas and Mexico. The tree is a living fossil that has twenty known extinct species, the oldest found in the Upper Eocene rocks of Greenland, during a time when the continent had a subtropical climate, some 55,000,000 years ago. Fossils were later found in Italy, Siberia, Colo., and in great numbers in the Miocene lake beds of Switzerland.

The tree gets its name from Native Americans and early pioneers who would chew its hard clumps of resin. This could be obtained by stripping off the bark and allowing the resin to harden. Commercial storax was used in fragrances and medicines as well and is found in related oriental sweet gum plants.

*Verbascum* (Mullein)

The Mulleins, of the genus *Verbascum*, are a genus of about 250 species of flowering plants in the figwort family (Scrophulariaceae). They are native to Europe and Asia, with the highest species diversity in the Mediterranean region.

They are biennial or perennial plants, rarely annuals or subshrubs, growing to 0.5-3 m tall. The plants first form a dense rosette of leaves at ground level, subsequently sending up a tall flowering stem. The leaves are spirally arranged, often densely hairy, though glabrous (hairless) in some species. The flowers have five symmetrical petals; petal colours in different species include yellow (most common), orange, red-brown, purple, blue or white. The fruit is a capsule containing numerous minute seeds.

*Eucalyptus*

The decongestant properties of *Eucalyptus* have been noted by the World Health Organization. Aetheroleum Eucalypti is the essential oil obtained by steam distillation and rectification of the fresh leaves or terminal branchlets of *Eucalyptus globulus* Labill (Myrtaceae) or other *Eucalyptus* species rich in 1,8-cineole. A clinical trial without controls assessed the effects of Aetheroleum Eucalypti as a nasal decongestant in 31 healthy volunteers. Inhalation of the essential oil (10 ml) over a period of 5 minutes had no effect on nasal resistance to airflow. However, the oil had a stimulant or sensitizing effect on nasal cold receptors, and the majority of subjects reported a sensation of increased airflow. A single-blind, parallel clinical trial assessed the efficacy of vaporized essential oil, camphor, menthol or steam in reducing nasal congestion in 234 patients with acute respiratory tract infections. The essential oil was significantly more effective in reducing nasal congestion only during the first hour following treatment (P<0.02) (32). In other clinical studies of patients with acute common colds, no significant differences in nasal decongestant activity were reported between the essential oil (1.3%) in petrolatum and a petrolatum placebo. WHO MONOGRAPHS ON SELECTED MEDICINAL PLANTS—Volume 2: Aetheroleus (2010).

SUMMARY OF THE INVENTION

The Inventor has experimented for years with combinations of herbs for use to treat his wife who suffers from emphysema and he has discovered such combinations, as claimed herein, with herbs contributing therapeutically to her vigorous well being, in spite of her inability to discontinue smoking cigarettes. This inventor has discovered a pulmonary restorative composition for improving respiratory health comprising an effective amount of *Gnaphalium obtusifolium* L., more commonly known as rabbit tobacco, sweet everlasting and other historical names; *Liquidambar*, more commonly known as sweet gum; and *Verbascum*, more commonly known as mullein. Optionally, the composition may include at least of one additional herbal nutrient selected from the group *Prunus avium*, more commonly known as wild cherry; *Althaea officinalis*, more commonly known as marshmallow or mallow; *Prunus amygdalus*, more commonly known as peach; and *Eucalyptus*; and may include glucose.

Most specifically, *Gnaphalium obtusifolium* L. is in the form of leaves and flowers of *Gnaphalium obtusifolium* plant, *Liquidambar* is in the form of the inner bark of *Liquidambar* tree, *Verbascum* is in the form of the leaves of *Verbascum* plant and the *Prunus avium* if present, is in the form of the inner bark of the *Prunus avium* tree, *Althaea officinalis*, if present, is in the form of the root of the plant, *Prunus amygdalus*, if present, is in the form of the leaves and bark of the *Prunus amygdalus* tree, and *Eucalyptus*, if present, is in the form of an extract of the leaves and stems of the *Eucalyptus* plant These herbs are found by numerous herbal manufacturers and distributors well known to those of ordinary skill in the art including such Internet advertised companies as Gryffon, Dragon & Wolf of Aptos, Calif., US, and Hope for Health, LLC, of Dallas, Tex., US.

According to one aspect of the invention a composition is provided comprising a pharmaceutically acceptable combination of the composition and at least one carrier. Pharmaceutically acceptable carriers for inclusion into the present compositions include carriers most suitable for combination with lipid-based drugs such as diluents, excipients and the like which enhance its oral administration. Suitable carriers include, but are not limited to, sugars, starches, cellulose and derivatives thereof, wetting agents, lubricants such as sodium lauryl sulfate, stabilizers, tableting agents, anti-oxidants, preservatives, coloring agents and flavoring agents. Reference may be made to REMINGTON: THE SCIENCE AND PRACTICE OF PHARMACY (REMINGTON THE SCIENCE AND PRACTICE OF PHARMACY) $21^{st}$ Edition, by University of the Sciences in Philadelphia (2005) for other carriers that would be suitable for combination with the present compositions. As will be appreciated, the pharmaceutical carriers used to prepare compositions in accordance with the present invention will depend on the administrable form to be used.

According to one embodiment of the invention, the novel composition of the present invention comprises, and is formulated for oral administration. Oral dosage forms formulated in accordance with standard pharmaceutical practice may be employed. Capsules are a particularly useful vehicle for administering the present composition. The administration of the composition is preferably in accordance with a predetermined regimen, which may be at least once daily and over an extended period of time as a chronic treatment, and could last for one year or more, including the life of the host. The dosage administered will depend upon administration frequency, and the blood level desired.

According to an additional embodiment, the compositions of the present invention may be admixed by conventional methods and may be administered by an alternative route such as suppository, spray, liquid, powder, liposome, dermal patch, and inhalant. These methods are well known to those skilled in the art. For example, liposomes may be formulated according to methods such as those of U.S. Pat. No. 5,853,755, to Foldvari, U.S. Pat. No. 4,235,871 to Papahadjopoulos, et al, or U.S. Pat. No. 4,708,861 to Popescu et al (liposome-gel combination). Sublingual and transdermal methods are also well known to those skilled in the art, e.g., U.S. Pat. No. 5,922,342 to Shah, et al describes a sublingual formulation and U.S. Pat. No. 4,997,655 to Nagy, et al describes a transdermal administration method.

DETAILED DESCRIPTION OF INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

In the Summary of the Invention above, the Description of the Invention, and the Claims and Abstract below, reference may be made to particular features, including method steps, of the invention. It is to be understood that this disclosure includes possible combinations of such particular features. For example, where a particular feature is disclosed in the context of a particular aspect or embodiment of the invention, or a particular claim, that feature may also be used, to the extent possible, in combination with and/or in the context of other particular aspects and embodiments of the invention, and in the invention generally.

The term "comprises" and grammatical equivalents thereof are used herein to mean that other components, ingredients, steps etc. are optionally present. For example, an article "comprising" (or "which comprises") components A, B and C can consist of (i.e. contain only) components A, B and C, or can contain not only components A, B and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number or the indefinite article a is used herein to denote the start of a range beginning with that number (which may be a range having an upper limit or no upper limit, depending on the variable being defined). For example "at least one" or at least a means 1 or more than 1. The term "at most" followed by a number is used herein to denote the end of a range ending with that number (which may be a range having 1 or 0 as its lower limit or a range having no lower limit, depending upon the variable being defined). For example, "at most 4" means 4 or less than 4, and "at most 40%" means 40% or less than 40%. If, in this disclosure, a range is given as "(a first number) to (a second number)" or "(a first number)-(a second number)", this means a range whose lower limit is the first number and whose upper limit is the second number. For example, 0-10 mm means a range whose lower limit is 0 mm, and whose upper limit is 10 mm.

The term "extract" is used herein as a concentrated preparation of a drink obtained by removing the active constituents of the drink with suitable solvents, evaporating all or nearly all of the solvent, and adjusting the residual mass or powder to the prescribed standard.

In its first preferred embodiment of the pulmonary restorative composition comprises *Gnaphalium obtusifolium* L. in an amount ranging from about 30 mg to about 3000 mg, *Liquidambar* in an amount ranging from about 50 mg to about 5000 mg, and *Verbascum* in an amount ranging from about 10 mg to about 1000 mg. In another more specific embodiment, the pulmonary restorative composition comprises *Gnaphalium obtusifolium* L. in an amount ranging from about 100 mg to about 1000 mg, *Liquidambar* in an amount ranging from about 150 mg to about 1500 mg, and *Verbascum* in an amount ranging from about 30 mg to about 300 mg. In its most specific form of this embodiment, the pulmonary restorative composition comprises *Gnaphalium obtusifolium* L. in an amount ranging of about 300 mg, *Liquidambar* in an amount of about 550 mg, and *Verbascum* in an of about 100 mg.

In yet another embodiment, the pulmonary restorative composition further comprises at least of one additional herbal nutrient selected from the group *Prunus avium, Althaea officinalis, Prunus amygdalus*, and *Eucalyptus*. The composition may also comprise glucose, used in manufacturing as an excipient. In yet another embodiment the pulmonary restorative composition comprises *Gnaphalium obtusifolium* L. in an amount ranging from about 30 mg to about 3000 mg, *Liquidambar* in an amount ranging from about 50 mg to about 5000 mg, and *Verbascum* in an amount ranging from about 10 mg to about 1000 mg, *Prunus avium* if present, in an amount of about 90 mg to about 6000 mg, *Althaea officinalis*, if present, in an amount of about 15 mg to about 1500 mg, *Prunus amygdalus*, if present, in an amount of about 5 mg to about 5000 mg, and the *Eucalyptus*, if present, in an amount of about 4 mcg to about 400 mcg. More specifically, the pulmonary restorative composition comprises *Gnaphalium obtusifolium* L. in an amount ranging from about 100 mg to about 1000 mg, *Liquidambar* in an amount ranging from about 150 mg to about 1500 mg, and *Verbascum* in an amount ranging from about 30 mg to about 300 mg, *Prunus avium* if present, in an amount of about 300 mg to about 3000 mg, *Althaea officinalis*, if present, in an amount of about 50 mg to about 500 mg, *Prunus amygdalus*, if present, in an amount of about 150 mg to about 1500 mg, and *Eucalyptus*, if present, in an amount of about 10 mcg to about 100 mcg. In its most specific form of this embodiment, the pulmonary restorative composition comprises *Gnaphalium obtusifolium* L. in an amount ranging of about 300 mg, *Liquidambar* in an amount of about 550 mg, and *Verbascum* in an of about 100 mg and *Prunus avium* if present, in an amount of about 1000 mg, *Althaea officinalis*, if present, in an amount of about 500 mg, the *Prunus amygdalus*, if present, in an amount of about 500 mg, and *Eucalyptus*, if present, in an amount of about 40 mcg.

In its most specific embodiment, the pulmonary restorative composition comprises *Gnaphalium obtusifolium* L. present in an amount ranging of about 300 mg, *Liquidambar* present in an amount of about 550 mg, and *Verbascum* present in an of about 100 mg, *Prunus avium*, present in an amount of about 1000 mg, *Althaea officinalis* in an amount of about 500 mg, *Prunus amygdalus* present in an amount of about 500 mg, and *Eucalyptus present* in an amount of about 40 mcg, and glucose present in an amount of about 3000 mg.

In another embodiment, the herbs are described by volume rather than by weight. In this embodiment, the pulmonary restorative composition comprises *Gnaphalium obtusifolium* L. in an amount ranging from about 0.2 ml to about 20 ml, *Liquidambar* in an amount ranging from about 0.2 ml to about 20 ml, and *Verbascum* in an amount ranging from about 30 mcL to about 3 ml. More specifically, the pulmonary restorative composition comprises *Gnaphalium obtusifolium* L. in an amount ranging from about 0.7 ml to about 70 ml, *Liquidambar* in an amount ranging from about 0.7 ml to about 70 ml, and *Verbascum* in an amount ranging from about 0.1 mL to about 1 mL. Most specifically the *Gnaphalium obtusifolium* L. is in an amount ranging of about 2.25 ml, *Liquidambar* is in an amount of about 2.25 ml, and *Verbascum* is in an of about 0.3 ml.

When the volume expressions are used, the pulmonary restorative composition may further comprise at least of one additional herbal nutrient selected from the group *Prunus avium, Althaea officinalis, Prunus amygdalus*, and *Eucalyptus*; and may also comprise glucose used in manufacture as an excipient. In one embodiment, the pulmonary restorative composition comprises *Gnaphalium obtusifolium* L. in an amount ranging from about 0.2 ml to about 20 ml, *Liquidambar* in an amount ranging from about 0.2 ml to about 20 ml, *Verbascum* in an amount ranging from about 30 mcL to about 3 ml and *Prunus avium* if present, in an amount of about 0.2 ml to about 20 ml, *Althaea officinalis*, if present, in an amount of about 15 mcL to about 1.5 mL, *Prunus amygdalus*, if present, in an amount of about 0.2 mL to about 20 mL, and *Eucalyptus*, if present, in an amount of about 4 mcL to about 400 mcL. More specifically, the pulmonary restorative composition may comprise *Gnaphalium obtusifolium* L. in an amount ranging from about 0.7 ml to about 70 ml, *Liquidambar* in an amount ranging from about 0.7 ml to about 70 ml, *Verbascum* in an amount ranging from about 0.1 mL to about 1 mL and *Prunus avium* if present, in an amount of about 0.7 to about 70 mL, *Althaea officinalis*, if present, in an amount of about 50 mcL to about 0.5 mL, *Prunus amygdalus*, if present, in an amount of about 0.7 to about 70 mL, and *Eucalyptus*, if present, in an amount of about 15 mcL to about 150 mcL.

In its most specific embodiment by volume amounts, the pulmonary restorative composition comprises *Gnaphalium obtusifolium* L. present in an amount ranging of about 2.25 mL, *Liquidambar* present in an amount of about 2.25 mL, and *Verbascum* present in an of about 2.25 mL, *Prunus avium* present in an amount of about 2.25 mL, *Althaea officialis* in an amount of about 2.25 mL, *Prunus amygdalus* present in an amount of about 2.25 mL, and *Eucalyptus* present in an amount of about 40 mcL, and glucose present in an amount of about 3.5 mL.

In yet another embodiment, the pulmonary restorative composition is expressed as percent of volume. In this embodiment, *Gnaphalium obtusifolium* L. is in an amount ranging of about 15% to about 80% by volume, *Liquidambar* is in an amount of about 15% to about 80% by volume, and *Verbascum* is in an of about 1% to about 10% by volume. More specifically, the pulmonary restorative composition comprises *Gnaphalium obtusifolium* L. in an amount of about 45% by volume, *Liquidambar* in an amount of about 45% by volume, and *Verbascum* in an amount of about 10% by volume.

In another embodiment, at least one of the optional herbs may be used and in one example of this embodiment of the pulmonary restorative composition *Gnaphalium obtusifolium* L. may be in of about 5% to about 45% by volume, *Liquidambar* may be in an amount of 5% to about 45% by volume, *Verbascum* may be in an of about 2% by volume, *Prunus avium* may be in an amount of about 5% to about 45% by volume, *Althaea officinalis* may be in an amount of about 5% to about 45% by volume, *Prunus amygdalus* may be in an amount of about 5% to about 45% by volume, *Eucalyptus* may be in an amount of about 0.1 to about 2% by volume, and glucose may be in an amount of about 5% to about 45% by volume. More specifically, *Gnaphalium obtusifolium* L. may be in of about 15% by volume, *Liquidambar* may be in an amount of 15% by volume, *Verbascum* may be in an of about 2% by volume, *Prunus avium* may be in an amount of about 15% by volume, *Althaea officinalis* may be in an amount of about 1% by volume, *Prunus amygdalus* may be in an amount of about 15% by volume, *Eucalyptus* may be in an amount of about 0.2% by volume, and the glucose in an amount of about 20% by volume.

Also taught by this inventor are methods for restoring pulmonary function in a human by administering an effective amount of the pulmonary restorative composition to a patient in need of treatment thereof. The administration may be in the amount of one to three tablespoons per dose, administered one to three times per day, most specifically the administration is in one tablespoon administered three times per day. The administration may be performed until pulmonary function is restored or for the remaining life of the human. The method may be useful for restoring pulmonary function wherein the pulmonary function is impaired by constricted bronchial tubes whether than constriction is the result of chronic obstructive pulmonary disease, asthma, infectious bronchitis, or emphysema. These methods may be useful in the treatment of any mammal in need thereof, most specifically, a human.

These methods may also be employed to preserve pulmonary function in mammals, especially humans, who are at risk of suffering dysfunction such as those who work with industrial chemicals and smokers.

The invention has been described in detail with particular reference to preferred embodiment thereof. However, it will be appreciated that those skilled in the art, upon consideration of this disclosure may make variations and modifications within the spirit and scope of the invention.

What is claimed is:

1. A method for restoring pulmonary function in a mammal in need thereof comprising administering to the mammal an effective amount of a pulmonary restorative composition, wherein the composition comprises:
   *Gnaphalium obtusifolium* L. present as leaves and flowers in an amount ranging from about 30 mg to about 3000 mg, *Liquidambar* present as inner bark in an amount ranging from about 50 mg to about 5000 mg, *Verbascum* present as leaves in an amount ranging from about 10 mg to about 1000 mg, and
   at least one additional herbal nutrient selected from the group consisting of *Prunus avium* present as inner bark in an amount of about 90 mg to about 6000 mg, *Althaea officinalis* present as root in an amount of about 15 mg to about 1500 mg, *Prunus amygdalus* present as leaves and bark in an amount of about 5 mg to about 5000 mg, and *Eucalyptus* present as leaves and stems in an amount of about 4 mcg to about 400 mcg.

2. The method of claim 1, wherein said administration is provided as a liquid dosage formulation in an amount of one to three 15 ml tablespoons per dose, administered one to three times per day.

3. The method of claim 1, wherein said administration is in one 15 ml tablespoon administered three times per day, said *Gnaphalium obtusifolium* L. is present in an amount of about 300 mg, said *Liquidambar* is present in an amount of about 550 mg, said *Verbascum* is present in an of about 100 mg, said *Prunus avium* if present, is present in an amount of about 1000 mg, said *Althaea officinalis*, if present, is present in an amount of about 500 mg, said *Prunus amygdalus*, if present, is present in an amount of about 500 mg, and said *Eucalyptus*, if present, is present in an amount of about 40 mcg.

4. The method of claim 3, wherein said mammal is a human.

5. The method of claim 4, wherein said administration is performed until pulmonary function is restored or for the remaining life of said human.

6. A method for preserving pulmonary function in a human who is at risk of suffering pulmonary dysfunction comprising administering to the human an effective amount a pulmonary restorative composition, wherein the composition comprises:
   *Gnaphalium obtusifolium* L. present as leaves and flowers in an amount ranging from about 30 mg to about 3000 mg, *Liquidambar* present as inner bark in an amount ranging from about 50 mg to about 5000 mg, *Verbascum* present as leaves in an amount ranging from about 10 mg to about 1000 mg, and
   at least one additional herbal nutrient selected from the group consisting of *Prunus avium* present as inner bark in an amount of about 90 mg to about 6000 mg, *Althaea officinalis* present as root in an amount of about 15 mg to about 1500 mg, *Prunus amygdalus* present as leaves and bark in an amount of about 5 mg to about 5000 mg, and *Eucalyptus* present as leaves and stems in an amount of about 4 mcg to about 400 mcg.

7. The method of claim 6, wherein said human works with industrial chemicals.

8. The method of claim 6, wherein said human is a smoker.

* * * * *